United States Patent [19]
Waits et al.

[11] Patent Number: 5,336,259
[45] Date of Patent: Aug. 9, 1994

[54] ASSEMBLY OF HEART VALVE BY INSTALLING OCCLUDER IN ANNULAR VALUE BODY

[75] Inventors: C. Thomas Waits, Pflugerville; Jonathan C. Stupka, Austin; T. Scott Peters, Georgetown; Alan S. Schwartz, Austin, all of Tex.

[73] Assignee: Carbon Implants, Inc., Austin, Tex.

[21] Appl. No.: 14,200

[22] Filed: Feb. 5, 1993

[51] Int. Cl.⁵ .............................................. A61F 2/24
[52] U.S. Cl. .................................... 623/2; 623/901; 29/890.124; 29/283.5
[58] Field of Search ............................ 623/2, 900, 901; 29/890.12, 890.124, 890.125, 890.13, 283.5; 137/512.1

[56] References Cited

U.S. PATENT DOCUMENTS

| | | | |
|---|---|---|---|
| 3,476,143 | 11/1969 | Kaster | 137/527.8 |
| 3,835,475 | 9/1974 | Child | 623/2 |
| 3,903,548 | 9/1975 | Nakib . | |
| 4,276,658 | 7/1981 | Hanson et al. . | |
| 5,152,785 | 10/1992 | Bokros et al. | 623/2 |

FOREIGN PATENT DOCUMENTS

0055406  3/1985  European Pat. Off. .

*Primary Examiner*—Randall L. Green
*Assistant Examiner*—D. Willse
*Attorney, Agent, or Firm*—Fitch, Even, Tabin & Flannery

[57] ABSTRACT

A method of making a prosthetic heart valve having an occluder which is supported to pivot between open and closed positions in an annular valve body made of pyrocarbon or a pyrocarbon-coated substrate. The valve body contains diametrically opposed pivot supports formed on the interior surface thereof and is distended by subjecting it to diametrically opposed compressive forces of a nature which place extensive exterior regions of the valve body in compression while increasing the distance between the pivot supports. After the occluder is installed in the distended annular valve body, removal of the opposed compressive forces permits the valve body to return to an unstressed, generally circular configuration with the occluder operatively secured between the pivot supports. These forces are applied using flexible, inextensible cables or resilient pressure pads.

19 Claims, 3 Drawing Sheets

ASSEMBLY OF HEART VALVE BY INSTALLING OCCLUDER IN ANNULAR VALUE BODY

The present invention relates to the manufacture of heart valve prostheses, and more particularly, to a method for installing one or more pivotable occluders in the valve body of a prosthetic heart valve.

BACKGROUND OF THE INVENTION

Various types of heart valve prostheses have been developed which operate hemodynamically as a result of the pumping action of the heart. Such heart valves include valves having single occluders which pivot along an eccentric axis (or both pivot and translate), to open and close the blood flow passageway, such as those described in U.S. Pat. Nos. 3,546,711, 4,011,601, 4,425,670 and 4,725,275, and also include bi-leaflet heart valves, such as those described in U.S. Pat. Nos. 4,078,268, 4,159,543, 4,254,508, 4,276,658, 4,328,592, and 4,535,484. The above-mentioned patents illustrate a variety of different arrangements for pivotally interconnecting valve members (i.e. occluders) and valve bodies.

In recent years, hi-leaflet heart valves have generally become the mechanical valve of choice. A bi-leaflet valve typically includes a valve body or orifice ring in which occluder means is in the form of a pair of leaflets which are pivotally mounted so as to alternately open to permit blood to flow in the downstream direction and close in response to backflow in the upstream direction. The outer surface of the valve body often has an annular channel which receives a metal stiffener ring which can be used for interconnecting with and supporting a sewing ring.

Commonly used bileaflet heart valves generally include two leaflets pivotally mounted by integral, laterally extending ears within recesses formed in a valve body which provides a conduit or central passageway for blood flow. The leaflets pivot open in response to hemodynamic pressure during the pumping stroke of the heart and then quickly pivot closed, as soon as the heart muscles relax the pumping chamber, to prevent substantial regurgitation of blood. The valve bodies, sometimes referred to as orifice rings, are principally manufactured using materials, such as pyrolytic carbon or pyrolytic carbon-coated graphite, which have sufficient resiliency to permit distension.

The valve body of a typical hi-leaflet heart valve prosthesis is generally annularly shaped, having an interior passageway with a generally circular cross-section except where a pair of diametrically opposed flat wall sections truncate the passageway at diametrically opposed secants along its periphery. The leaflets engage diametrically opposed pivot supports that are integrated within each of the flat wall sections.

The method used most commonly for installing leaflets in a valve body is to deform the valve body so that the pivot supports are spread far enough apart to permit the leaflets to be installed. For example, the valve body may be squeezed or may be distended by the application of force to interior surfaces thereof. This method is possible because pyrolytic carbon can be elastically deformed within limits, and as soon as the distending force is removed, the valve body returns to its cylindrical or annular shape, wherein the inserted leaflets are secured in the pivot supports. After the leaflets are installed, a stabilizing ring, as is well known in the art, may be shrunk-fit about the exterior surface of the valve body so as to stabilize the valve body and assure that it retains its precise generally circular cross-sectional configuration.

One specific method for installing leaflets in a valve body is to insert sets of pins within an orifice ring so that the pins engage the inside flat surfaces defining the passageway, and then spread the pins apart with sufficient forces to deform or elongate the orifice ring in order to provide clearance to install the leaflets. After the leaflets are appropriately positioned between the pivot supports, the pins are retracted so that the orifice ring returns to its original annular configuration and the pivot supports engage and secure the leaflets.

As a result of subjecting valve bodies to forces necessary to spread the pivot supports apart, the pyrolytic carbon structures or coatings of many valve bodies develop cracks. Some of these cracks are large enough to be detected with the naked eye. Valve bodies which develop such large cracks are immediately rejected; however, some of the pyrolytic carbon structures of other valve bodies have been known to develop very tiny, hairline cracks, called microcracks, which can be difficult to detect. Microcracks are undesirable because their long term effects on the structural integrity of a valve body are presently unknown. Microcracks which can be detected at the surface of a valve body generally result in rejection of the body during quality control inspection. However, some valve bodies may have microcracks beneath the exterior surface of the valve body that are not visible, and hence, are undetectable, absent destructive testing of the valve body. Consequently, there is a possibility that some heart valve prostheses having a pyrolytic carbon structure containing undetected microcracks may occasionally pass quality control inspections.

It has been felt that cracks develop in the pyrolytic carbon coatings or structures because the method by which the forces are commonly applied to the valve bodies can subject that pyrocarbon to stresses which exceed its the fracture stress limitations. Therefore, there is a need for a method for installing an occluder or a pair of leaflets into a heart valve prosthesis which does not cause cracks to develop in the pyrolytic carbon structures or coatings of such valve components.

SUMMARY OF THE INVENTION

The present invention provides a method for making heart valve prostheses by installing an occluder or a pair of leaflets in a valve body in a manner which does not cause cracks to develop in the valve body. The outer periphery of a valve body is subjected to compressive forces in such a manner so that these forces are distributed over relatively large surface areas of the valve body. Distributing the forces over such relatively large surface areas prevents the concentration of such forces in a way so that they would exceed the fracture stress limitations of the pyrolytic carbon materials comprising the valve body.

More specifically, the present invention provides a method of assembling a prosthetic heart valve having occluder means intended to pivot between open and closed positions in an annular valve body made of pyrocarbon or a pyrocarbon-coated substrate while being supported by diametrically opposed pivot supports formed on the interior surface of the valve body. The method comprises the steps of: elongating the valve body by subjecting the valve body to diametrically opposed compressive forces applied over a relatively large area of the exterior surface of such a valve body so as to increase the distance between the pivot supports; installing the occluder means in the annular valve body and removing the opposed compressive forces to permit the valve body to return to an annular configuration, whereby the occluder means is operatively interconnected with the pivot supports.

One advantage of the method of the present invention is that it provides a method for installing an occluder or a pair of leaflets in a valve body manufactured of a pyrolytic carbon structure or pyrolytic carbon coated structure in a manner which does not produce cracks in the pyrolytic carbon.

Another advantage of the present invention is that it provides a method by which a heart valve body may be safely elongated or distended to provide clearance to allow the installation of one occluder or a pair of leaflets within the valve body while subjecting the valve body to predetermined, consistently controlled compressive forces over relatively large surface areas which forces do not result in damage to the valve body.

BRIEF DESCRIPTION OF THE DRAWINGS

Throughout the specification and drawings, like components are referenced using like reference numerals.

DESCRIPTION OF THE PREFERRED EMBODIMENTS

The method of the present invention is particularly adapted for the manufacture of prosthetic heart valves of the type having one or more occluders, or leaflets which are designed to generally pivot while being supported in generally diametrically opposed pivot supports located within the passageway of an annular valve body in the form of an entirely pyrolytic carbon structure or a suitable substrate having a pyrocarbon coating thereon. In general, the method involves applying diametrically opposed forces upon extensive regions of the exterior circumference of the valve body, which forces are directed towards the center of the passageway, in order to compress the valve body in one direction and elongate it in a transverse direction. Equal and opposite forces are applied over a relatively wide area, i.e. across a pair of substantial arc/lengths on the exterior circumferential surface of the valve body and encompassing in the transverse direction a substantial or major portion of the axial length thereof, in a manner whereby the net resulting force acting on the valve body is substantially zero. Such application of forces causes the valve body to become elongated or distended in a direction transverse or perpendicular to the direction of the forces on the valve body, and to thereby provide clearance to install a single occluder or a pair of leaflets between the spread-apart pivot supports. Elongating the valve body in this particular way has been found to place a large portion of the valve body in compression and thereby avoid the generation of such stresses in the pyrolytic carbon which may cause cracking. After the valve body has been sufficiently elongated, the occluder or pair of leaflets are appropriately positioned within the passageway of the valve body in alignment with the pivot supports. Then, the compressive forces are gradually reduced so that the resilient valve body slowly returns to its original, annular shape, thereby securing the occluder or leaflets between generally diametrically opposed pivot supports.

Figures 1, 2:
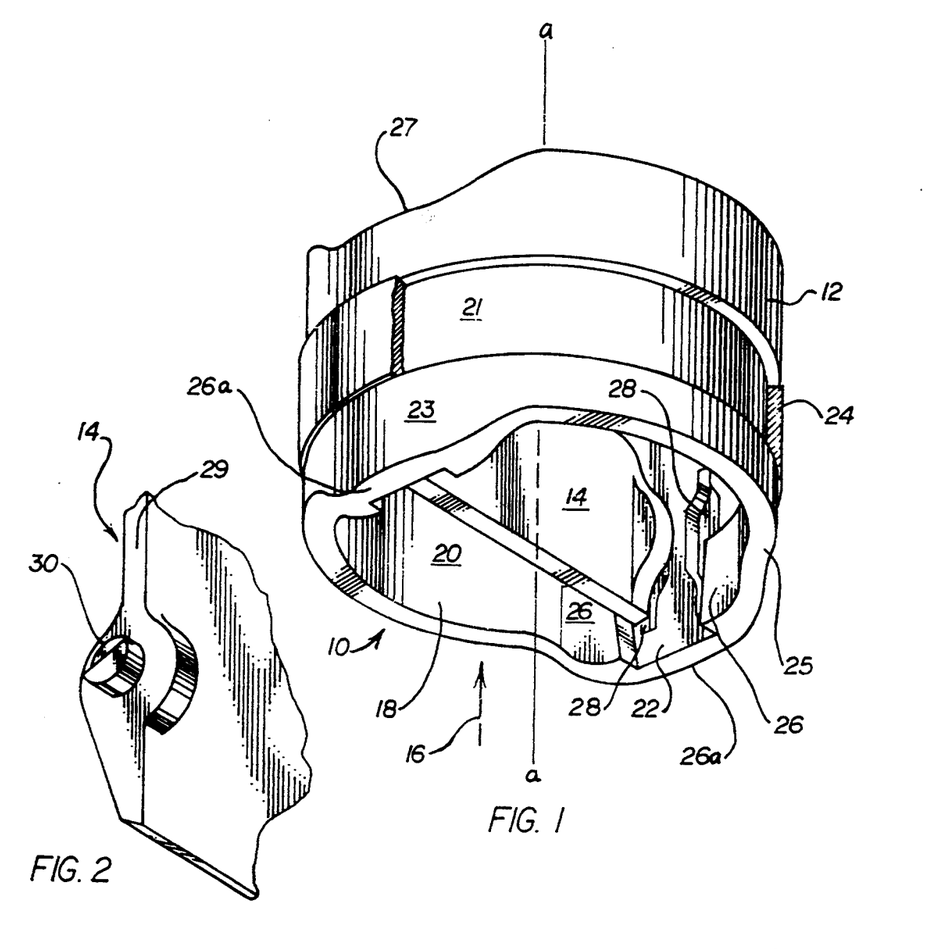
FIG. 1 is a perspective view of a representative bi-leaflet heart valve prosthesis showing (for purpose of illustration) only one leaflet installed in the valve body, which valve can be assembled in accordance with the method of the present invention.
FIG. 2 is a fragmentary perspective view of one side of a leaflet designed for mounting in the valve of FIG. 1.

The resilient pyrocarbon valve body needs to become elongated in a direction substantially parallel to the pivot axes of the leaflets, and thus the orientation of the valve body with respect to the direction of application of compressive forces is very important. Accordingly, an understanding of the method for installing a pair of leaflets in a heart valve prosthesis should be enhanced by describing this method with regard to an example of one particular prosthetic heart valve. The heart valve prosthesis, illustrated in FIGS. 1 and 2 is more particularly described in U.S. patent application Ser. No. 837,761, filed Feb. 18, 1992, the disclosure of which is hereby incorporated by reference. However, it is to be understood that the method of the invention may be generally employed for installing a single occluder or a pair of leaflets in any such heart valve prosthesis where the occluder or two leaflets are mounted by generally diametrically opposed engaging means carried by the valve body.

FIGS. 1–2 collectively show a prosthetic heart valve 10 including a generally annular valve body 12 supporting a pair of pivoting occluders or leaflets 14, only one of which is shown so as to better illustrate the mounting arrangement. The leaflets 14 open to allow the flow of blood in a downstream direction, as indicated by the arrow 16, and quickly close to prevent any substantial backflow of blood. The valve body 12 is annular and provides a central blood flow passageway 18 defined by a generally right circular cylindrical interior surface 20 which is interrupted by a pair of diametrically opposed flat wall sections 22. The passageway 18 through the annular valve body is thus generally circular in cross-section except for the two flat wall sections 22. The passageway 18 has a longitudinal centerline or axis a—a which is substantially parallel to the direction of blood flow.

A pivot arrangement for defining the opening and closing movements of the leaflets 14 includes elements formed as a part of the valve body 12 in the region of the flat wall sections 22, which elements engage and coact with corresponding elements formed as a part of each of the leaflets. The outer circumferential surface 23 of the valve body characteristically includes a shallow groove or channel 21 which ultimately receives a metal stiffening ring 24 that provides stability and rigidity to the valve body, which body is preferably made of a material having adequate resiliency when distended, such as pyrocarbon or pyrocarbon-coated graphite, as well known in this art. In addition to its outer, curvilinear circumferential surface 23, the valve body 12 has an upstream surface 25 at the inlet end of the passageway 18 and a downstream surface 27 at the outlet end of the passageway. For reference purposes, a plane perpendicular to the parallel interior flat surfaces 22 which includes the longitudinal axis a—a is referred to as the "centerline plane" throughout this specification.

By way of example, the valve body 12 may consist of a pyrolytic carbon coating formed over an underlying isotropic graphite substrate, or it may be made entirely of pyrolytic carbon manufactured in accordance with known techniques.

The illustrated pivot arrangement further includes four radially extending projections 26 formed in the upstream regions of the flat wall sections 22 which protrude radially inward from the interior surface of the valve body and which extend longitudinally into a pair of standards or extensions 26a that protrude longitudinally from the otherwise generally flat inflow surface 25 of the valve body. The radial projections 26 are arranged in two pairs, with one pair being diametrically opposed to the other and with the two projections of each pair individually generally flanking the upstream regions of the flat wall sections 22 of the valve body.

In addition to the projections 26, the pivot arrangement includes a pair of slots 28 formed in each flat wall section 22. The slots 28 are arranged so that, of each pair, one slot lies on each side of the centerline plane. Each leaflet 14 has a generally flat main body section and a pair of coaxial pegs 30 which extend laterally outward from lateral edge surfaces 29 on the sides of the leaflet. The pegs 30 are received in the slots 28 and coact therewithin as a part of the pivot arrangement.

The method of the present invention is directed to installing the leaflets in the valve body without generating cracks in the pyrolytic carbon which forms the structure or coating of the valve body. More particularly, the method of the present invention is first described with reference to FIGS. 3-5 where there is shown one such apparatus 40 for laterally elongating or distending the valve body 12 in order to facilitate installation of the leaflets 14. The operation of the apparatus 40 relies on applying diametrically opposed, compressive forces to relatively large exterior arcuate surface regions of the valve body 12 in order to elongate it and thereby provide spacial clearance to insert the leaflets between the engaging means, i.e. the slots 28 within the passageway 18. This apparatus 40 includes a lower positioning jig 44 which is suitably mounted upon a supporting base 45. The positioning jig 44 has an upper profiled surface which conforms to the corresponding surface of the valve body 12 so that the valve body may be stably supported in an appropriate position on the apparatus 40. In the illustrated embodiment, it conforms generally to the profile of the upstream surface 25 of the valve body (see FIG. 3); for example, the upper surface of the jig 44 may have an oversize groove 44a proportioned to receive the standards 26a so they can slidably move therein without touching the groove surface.

Figure 4:
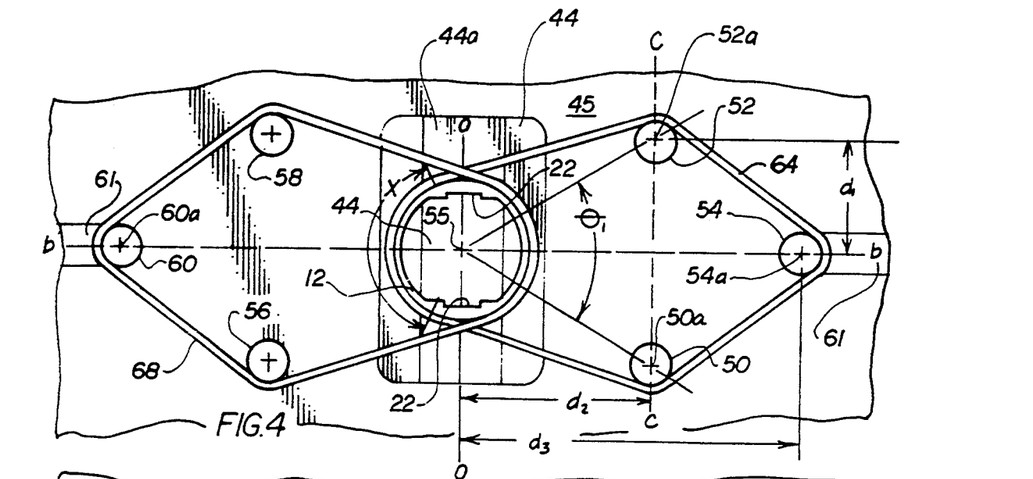
FIG. 4 is a schematic plan view of the apparatus of FIG. 3.

To apply the deforming force to the valve body, two sets of three pins each are provided. A first set of three roller pins 50, 52, and 54 is mounted upon the supporting base 45 on the righthand side of the jig 44 on which the valve body 12 is installed. The pins 50 and 52 are mounted and oriented so that they rotate about longitudinal axes substantially normal to the flat upper surface of the base 45; the pin 54 can optionally be rotatable, but need not be. A similar set of three roller pins 56, 58 and 60 is located on the lefthand side of the jig (FIG. 4). The center 55 of the jig 44 and the pins 54 and 60 are aligned along the longitudinal centerline b—b of the base 45. The three longitudinal axes 50a, 52a, and 54a of the pins 50, 52, and 54, respectively, define a triangle with the side of the triangle defined by the pins 50 and 52 being perpendicular to the centerline of the base.

In the preferred embodiment of the apparatus 40, the pins 50, 52, 56, and 58 are fixedly positioned on the surface of the fixture so that the angle $\theta$, defined by the axes 50a and 52a of the outboard pins and the center 55 of the jig 44, is bisected by the longitudinal centerline b—b which is defined by the axes of the pins 54, 60. For reasons which are explained further hereinafter, the distance, $d_1$, between each of the axes 50a and 52a of the pins 50 and 52 and the centerline b—b should be between about 60 to 100% of the length of the outside diameter of the valve body 12 and preferably between about 75% and 85% thereof. A reference line c—c, defined by the axes 50a and 52a, is perpendicular to and intersects the centerline b—b at a distance $d_2$ from the center of the jig (FIG. 4). The distance $d_2$ is preferably equal to between about 80 to about 200 percent of the length of the outside diameter of the valve body 12. The pattern of second set of three roller pins 56, 58 and 60 is symmetrical to that of the pins 50, 52 and 54.

While the outboard pins 50, 52, 56 and 58 are fixedly mounted upon the supporting base 45, the pins 54 and 60 are slidably mounted in slots 61 provided in the base structure and aligned with the centerline b—b in a manner which allows the pins 54 and 60 to be translated farther away from each other, along the reference line b—b, so that the distance between them is controllably increased from that shown in FIG. 4. Any suitable mechanism which spreads the pins can be employed. For example, the system can be manually controlled using a worm gear drive mechanism wherein the operator manually spreads the pins 54, 60 based on visual observation.

Figure 3:
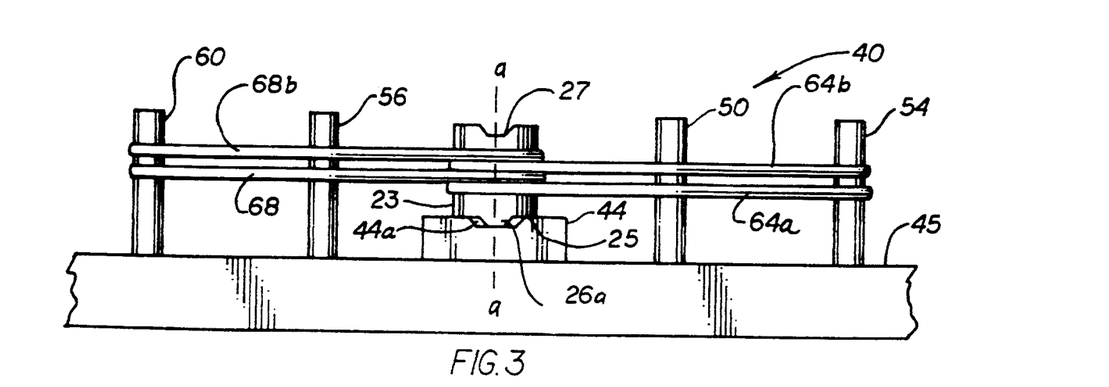
FIG. 3 is a front elevation view of one embodiment of an apparatus for distending a valve body of a heart valve prosthesis in accordance with a method incorporating various features of the present invention.

A first flexible, substantially inextensible cable member 64a is positioned to pass around the pins 50, 52 and 54 and to lie in arcuate contact within the groove 21 formed in the exterior surface 23 of a valve body 12, as shown in FIGS. 3 and 4. The offset distance $d_1$ between each pin center 50a, 52a and the line a—a and the distance $d_2$ are selected so as to allow the flexible endless cable member 64 to lie in contact the exterior circumferential surface 23 of the valve body 12 over a first arc length of about 90° to about 170°, and preferably the arc length is at least about 120°. Similarly, a second flexible cable member 68a is positioned about the pins 56, 58 and 60 and the groove 21 so that the flexible member 68a is in contact with the valve body about a second arc which is equal in length to the first arc length, e.g. at least about 120°, and located in a diametrically opposed region on the exterior surface of the valve body. The width or diameter of the flexible cable member 64 is about 25 percent of the width of the groove 21 of the valve body so that four cable members can be conveniently positioned about each valve body at one time. These first and second arc lengths of contact are located symmetrically about the centerline plane of the valve body 12, which plane is shown edge-on as line o—o in FIG. 4. Preferably, distances $d_1$ and $d_2$ are fixed to cause the arc length X (FIG. 4) of initial contact to be equal to or slightly greater than the length of the arcuate interior surface portion of the valve body lying between the flat wall surfaces 22, as measured in degrees. Cable length is a function of $d_3$ (FIG. 4), and $d_3$ may be any value greater than $d_2$; the greater the length of $d_3$, the more linear the relationship is between applied load and force.

By way of example, for human heart valves which may typically have outer diameters between about 16 mm and about 29 mm, the flexible cable members may be endless or continuous twisted wire cable loops each at least about 13 cm in length. They are preferably sheathed in a thin covering of nylon so as not to abrade the exterior of the valve body. Two additional cable loops 64b and 68b are then put in place above the first two loops so that there are four cables in all, as best seen in FIG. 3.

When the flexible members 64 and 68 are first positioned around the pins and the valve body on the jig 44, the positions of the translatable pins 54 and 60 are set inward toward each other such that there is very little initial tension in the flexible members 64, 68. This tension should merely provide enough frictional force between the flexible cable members and the pins, and between the flexible cable members and the valve body surface to hold the cables in position.

Although the pairs of flexible cable members 64a,b and 68a,b contact the outside periphery of the groove 21 along arc lengths which are diametrically opposed, they apply these forces at different axial locations (as can be seen from FIG. 3) so that the flexible members have a tendency to apply a net torque to the valve body 12 in a vertical plane which could twist the valve body off of the jig 44. The employment of two pairs of endless cable loops tends to cancel out most of the twisting; however, it may be desirable to build twist resistance into the positioning jig 44 so it more steadily supports the valve body 12 to assure that it remains in place.

Figure 5:
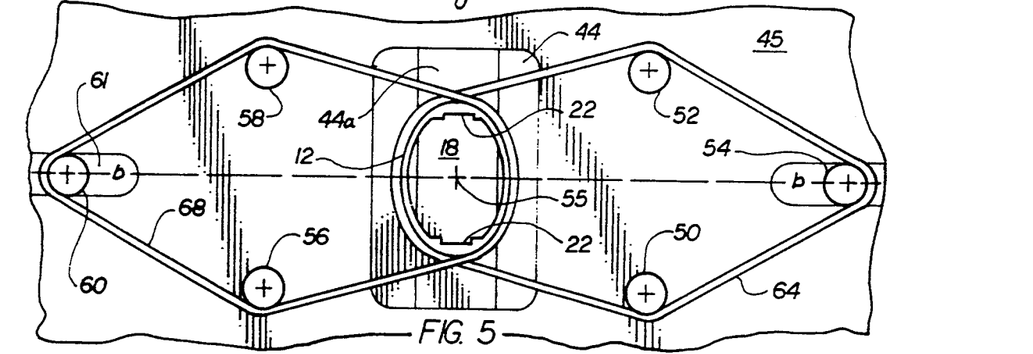
FIG. 5 is a schematic plan view similar to FIG. 4 showing the valve body following the application of force to distend it.

By mechanically spreading the pins 54 and 60 apart, the tension in each of the flexible cable members 64 and 68, which are substantially inextensible, is increased. It quickly results in the application of diametrically opposed forces to opposite arcuate regions of the external circumferential surface 23 of the valve body, which forces are inwardly directed and constitute composite forces focused generally toward the centerline a—a. The mechanical forces on the pins 54 and 60 can be generated in any suitable way, as by hydraulically actuating a cylinder connected between pin supports which move in the slots 61, or by connecting supports for the pins 54, 60 to a worm gear or lead screw. Such forces would increase, for example, as the hydraulic pressure in such a cylinder increased. These forces tend to place major portions of the valve body in compression, i.e. in the regions where there is contact with the cables, and they cause the normally annularly shaped valve body 12 to distend to become somewhat elliptically shaped, as shown in FIG. 5. This distension or elongation increases the distance between the diametrically opposed parallel flat surfaces 22 in which the slots 28 are formed.

Distension may be controlled as a function of force applied to spread the pins 54 and 60. This force may be measured as torque applied to a screw, or the hydraulic pressure in a cylinder. Alternatively, the direct force being applied may be measured using a load cell or using a strain gauge attached to one of the pins 54, 60. When the valve body 12 is sufficiently elongated, as depicted in FIG. 5, the leaflets 14 are inserted into position within the passageway 18, with one of the pegs 30 being first received within one of the slots 28, then aligning the other peg with the opposite slot and finally shifting the leaflet so both pegs partially reside in the respective slots. Next, the tension in the four flexible cable members 64a and b, and 68a and b is slowly reduced, for example, by decreasing the hydraulic pressure in the cylinder and thereby reducing the distance between the pins 54 and 60 along a path coincident with centerline b—b. As the tensions in the flexible cable members 64 and 68 are allowed to slowly decrease to about zero, the valve body 12 returns to its original annular shape, i.e. having a circular cross-section, with the pegs 30 on both sides of each leaflet 14 becoming securely entrapped within the slots 28. The valve body 12 with its installed leaflets 14 is then removed as an assembled unit from the positioning jig 44 by slipping the cables from around its outer surface.

Figure 6:
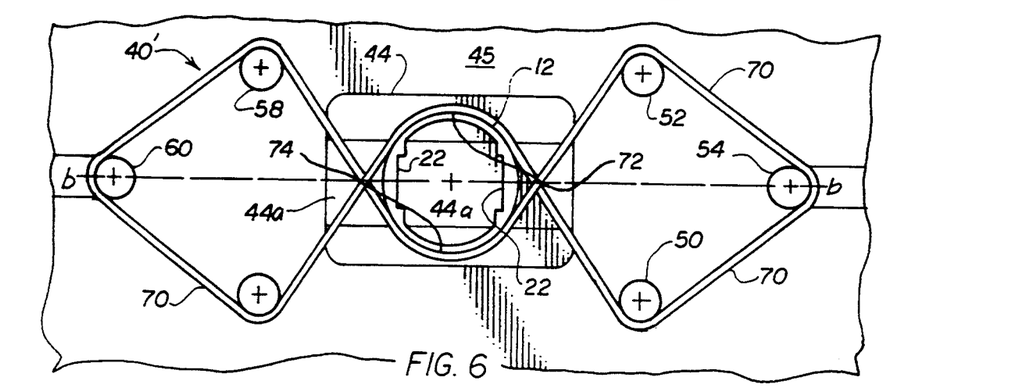
FIG. 6 is a schematic plan view of apparatus similar to that of FIGS. 3 and 4, but where a single endless flexible cable member is employed to distend the valve body.

As an alternative to using two flexible members 64a and 68a wrapped around the valve body in the region of the groove 21 to apply the forces which elongate the valve body 21, a single flexible cable member 70, as shown in FIG. 6, may instead be employed. The single flexible member 70 is an endless or continuous loop that is wrapped about the valve body and contacts it at two diametrically opposed locations 72 and 74; it is also threaded around the pins 50, 52, 54, 56, 58 and 60. It is to be noted that the arc lengths of contact between the flexible member 70 and the groove 21 are likewise diametrically opposed to each other and are also essentially symmetrical axially along the outer surface of the valve body, which arrangement allows one flexible cable member to be employed to take the place of two as in the arrangement shown in FIGS. 4 and 5. The positioning jig 44 in FIG. 6 is oriented at an angular position which is rotated 90° with respect to the angular position of the jig 44 in FIG. 4 so that the slot 44a is aligned with the centerline b—b of the base 45. As a result, when the valve body 12 is positioned in the positioning jig 44 and deflected by the cables, it becomes elongated in a direction along the centerline b—b of the base 45.

In order to accommodate potential twisting of the flexible cable member 70, the flexible cable preferably has a circular cross-sectional area. The flexible members 64 and 68 may also be circular in cross-section; however, they may also be flexible endless bands of rectangular cross section which are substantially inextensible and which preferably have a dimension equal at least about 10% of the height or axial length of the main body of the valve body.

Installation of the leaflets 14 into the valve body 12 in the case where at least one flexible member 70 is employed in conjunction with an apparatus 40' in FIG. 6 is virtually identical to the case described above in which the flexible members 64, 68 are used. After placing a valve body 12 in the positioning jig 44, the flexible member 70 is wrapped around the outside surface 23 of the valve body, twisted twice, in opposite directions, and then threaded outside of the six pins as shown in FIG. 6. If desired, a second cable 70 can be similarly installed above the first. Then, tension is applied as before to the flexible but substantially inextensible cable member 70 to distend the valve body 12 by applying force which increases the distance between the pins 54 and 60 until the valve body becomes sufficiently elongated to allow the leaflets 14 to be inserted into the passageway 18 so that the pegs 30 are received within the slots 28 formed in the flat surfaces 22 as described hereinbefore. The tension in the flexible member 70 then is slowly reduced to about zero in order to allow the valve body 12 to return to its original annular shape. Such a decrease in the tension of the flexible member 70 results from decreasing the distance between the pins 54, 60. When the flat surfaces 22 to return to their normal locations in the unstressed annular valve body, the slots 28 securely entrap the pegs 30, securing the leaflets within the valve body 12.

Figure 7:
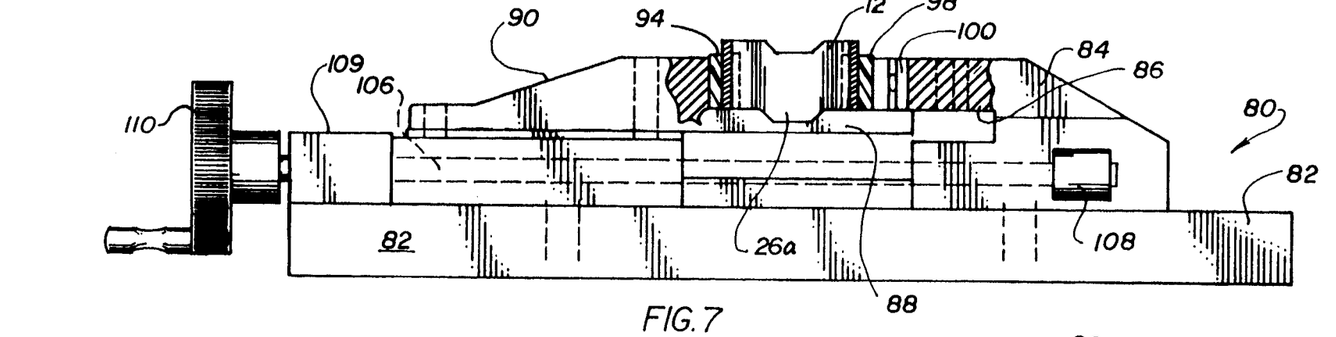
FIG. 7 is a front elevation view of another apparatus for distending a valve body of a heart valve prosthesis in accordance with an alternative method of assembly embodying various features of the present invention, with a small portion being in section taken generally along the line 7—7 of FIG. 8.
Figure 8:
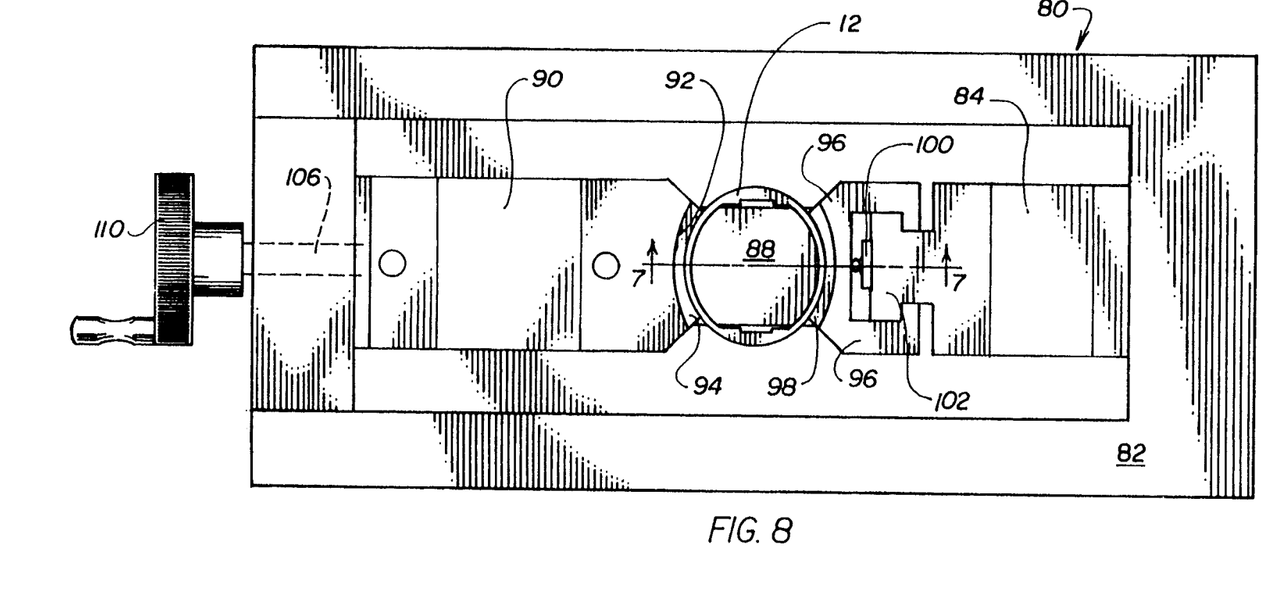
FIG. 8 is a plan view of the apparatus of FIG. 7.

FIGS. 7 and 8 depict another apparatus 80 which may be employed to elongate a valve body 12 without the introduction of cracks to facilitate installation of the leaflets 14 between the pivot supports or slots 28 within the walls which define the passageway 18. In FIG. 7, there is shown apparatus 80 that includes a supporting base structure 82 on which is mounted a stationary positioning fixture or jig 84 near the righthand end of the base as viewed in FIG. 7. The stationary jig 84 is provided with an undercut 86 which receives the forward end 88 of a slide adapter 90 that carries the other half of the force-applying unit. More specifically, the slide adapter 90 is shaped, as best seen in FIG. 8, to provide a slightly curved surface 92 having approximately the curvature of the distended outer surface of a valve body that has been deformed to the amount of elongation sufficient to insert the leaflets. A resilient pad 94 made of a suitable material, such as polyurethane or synthetic rubber having a durometer of about 70 to 90 and having a thickness of at least about 0.05 inch, is mounted on the slide adapter 90 against the curved surface 92 where it will engage the exterior sidewall of a valve body 12 positioned against the stationary jig 84 and resting on the forward end section 88 of the slide adapter. In this respect, the width of the forward end 88 of the slide adapter is proportioned so that it is received between the pair of standards 26a that project from the otherwise flat inflow surface of the valve body.

A pressure plate 96 of similar curvature to the front surface 92 of the slide adapter is connected to the stationary fixture 84, and it supports a resilient pressure pad 98 of similar dimensions to the pad 94 described hereinbefore. The pressure plate 96 is preferably loosely mounted on the upper end of the fixture so that a load cell 100 is located between the rearward facing surface of the pressure plate 96 and the front of an upper backing plate portion 102 of the fixture, as a result of which construction, the load cell 100 provides a measurement of the amount of force being exerted by the pressure plate 96 against the valve body through the resilient pad 98 at any instant.

In the illustrated embodiment, a long lead screw 106 runs longitudinally of the base 82 of the apparatus it is connected at its righthand end to a thrust bearing 108 and carries a hand wheel 110 at its lefthand end adjacent a rear bearing 109. The slide adapter 90 is appropriately operably interconnected to the lead screw 106 by a pair of nuts (not shown) so that it travels either forward or rearward along the screw depending upon whether the hand wheel 110 is being turned clockwise or counterclockwise.

For the installation of a pair of leaflets in a valve body, the valve body is located, inflow end down, upon the front end 88 of the slide adapter, positioned against the resilient pad 98 carried by the stationary fixture 84. The hand wheel 110 is then turned clockwise so as to cause the slide adapter 90 to advance along the screw with its front end 88 sliding under the undercut 86 and causing the resilient pad 94 to also firmly engage an arcuate region of the exterior of the valve body. As the hand wheel is continued to be slowly turned, the opposing resilient pads 94, 98 apply compressive forces against diametrically opposite, relatively large regions of the exterior of the valve body. The force from the apparatus 80 is transferred from the curved surfaces of the slide adapter 90 and the pressure plate 96 through the resilient pads to the exterior surface of the valve body. The forces are applied symmetrically about the centerline plane of the valve body, and the resilient yet relatively rigid urethane pressure pads of 70–90 durometer effectively spread the force across arcuate regions which preferably each have an arc length of at least about 120° and a height or axial length equal to a major portion, e.g. at least about 40%, and preferably at least about half that of the valve body, thus placing these major regions of the valve body in compression while the valve body is being sufficiently elongated to provide clearance to insert the leaflets as explained hereinbefore. The location of the load cell 100 between the backing plate and the pressure plate provides a constant indication of the amount of force being applied at any instant; thus it allows the operator to quickly take the valve body to an elongation which is just sufficient to permit the installation of the leaflets.

It can be shown that, in pyrocarbon valve bodies of this type, the imposition of a certain amount of force will nearly always cause the same amount of distension or elongation in the direction transverse to the direction in which the force is applied. The curved backing surfaces and the resilient pads establish the application of substantially uniform compressive forces over a relatively broad surface area on the outer curvilinear surface of the valve body. As a result, these portions of the outer surface are placed in compression, and because pyrocarbon is substantially stronger in compression, this has the positive effect of preventing cracks from developing in the pyrolytic carbon structure of the valve body during the time of the distension to install the leaflets.

As described previously, the hand wheel 110 is turned clockwise until the compressive forces being applied cause the valve body to become sufficiently elongated to provide clearance to permit the installation of the pair of leaflets. Thereafter, following insertion of the leaflets, the hand wheel 110 is slowly turned counterclockwise to reduce the compressive force to zero, allowing the valve body to return to its original annular shape wherein the leaflets are firmly entrapped therewithin with the laterally extending pegs 30 being received in the slots 28 in the flat sidewall portions. The assembly of the leaflets within the valve body is then complete so that the assembled unit is removed and the next valve body is placed in position on the forward end of the slide adapter. It has been found that, by the application of compressive forces over a substantially large arcuate region of the exterior of a valve body, i.e. by pressing against a pair of regions at least about 60° in arc length, and preferably at least about 120° in arc length, a sufficient portion of the pyrolytic carbon valve body is placed in compression where its structural strength substantially increases so as to serve as a positive deterrent against the creation of cracks and thus greatly facilitating production and lowering the expense of manufacturing.

The foregoing descriptions include the best modes presently contemplated for practicing the invention; however, the description is not to be taken in a limiting sense, but is made for the purpose of describing the general principles of the invention. Although the invention has been described in terms of certain preferred embodiments, modifications obvious to one of ordinary skill in this art may be made without departing from the scope of the invention. For example, the invention is not limited to the assembly of valves having leaflets with laterally protruding ears, but it is likewise suitable for the assembly of valves utilizing an occluder or occluders having slots in the lateral edges that fit about engaging projections or the like. Likewise, the method of assembly is not limited to valve bodies having a pair of diametrically opposed flat surfaces, but it can equally be used to install circular disk occluders in valve bodies, such as shown in U.S. Pat. No. 4,240,161, Dec. 23, 1980. Similarly, the valve body need not have a groove in its exterior design to accommodate a stiffening ring or the like because the compressive forces can be applied to the exterior of the valve body regardless of whether such a shallow locator is formed in the exterior surface. Accordingly, the scope of the invention is to be determined with reference to the appended claims. The terms pyrolytic carbon and pyrocarbon are used interchangeably throughout, and by pyrocarbon valve body is meant a structure formed either entirely of pyrocarbon or a suitable substrate the exterior of which is coated with pyrocarbon, which pyrocarbon may include an alloy with a material such as silicon carbide as well known in this art.

Particular features of the invention are emphasized in the claims which follow.

What is claimed is:

1. A method of making a prosthetic heart valve having occluder means supported for movement between an open position and a closed position in an annular pyrocarbon valve body having an interior passageway of generally circular cross section for blood flow therethrough wherein engaging means on the interior surface of said valve body supports said occluder means for said movement, which method comprises distending said valve body by the application to the exterior surface of said valve body of two oppositely directed compressive forces, which forces are aligned along a diameter located essentially perpendicular to a line interconnecting said valve body engaging means, said forces being exerted over certain diametrically opposite arcuate surface regions of the exterior surface of said annular valve body each equal to at least about 60 degrees of arc so as to place said certain exterior surface regions in compression while distending said annular valve body from its unstressed generally circular configuration to cause said engaging means to move sufficiently far apart from each other to permit said occluder means to be installed, installing said occluder means in said distended valve body so as to be supported by said engaging means, and removing said oppositely directed compressive forces to permit said valve body to return to its unstressed generally circular configuration with said occluder means operatively supported therewithin.

2. A method in accordance with claim 1 wherein said compressive forces are applied to said exterior surface regions of said annular valve body by the use of flexible force-applying means.

3. A method in accordance with claim 2 wherein said flexible force-applying means includes flexible cable means.

4. A method in accordance with claim 3 wherein said flexible cable means is provided with a flat face which engages said exterior surface and has a height dimension of which is equal to at least about 10 percent of the height of said annular valve body.

5. A method in accordance with claim 3 wherein said cable means comprises two separate continuous bands.

6. A method in accordance with claim 3 wherein said cable means comprises a single flexible continuous band.

7. A method in accordance with claim 6 wherein said single flexible continuous band is placed in tension and is located to apply distributed compressive forces to the exterior of said valve body symmetrically about the axial centerline of said valve body passageway.

8. A method in accordance with claim 7 wherein said two symmetrically distributed compressive forces are applied to arcuate regions each equal to at least about 120 degrees of arc.

9. A method in accordance with claim 3 wherein said annular valve body has a circumferential groove formed in said exterior surface thereof, which exterior surface is otherwise generally that of a right circular cylinder, and wherein contact between said flexible cable means and said annular valve body occurs in said circumferential groove.

10. A method in accordance with claim 9 wherein said flexible cable means includes four flexible bands each being generally circular in cross-section.

11. A method in accordance with claim 9 wherein, following removal of said flexible cable means, a stiffening ring is shrink-fitted into place about the exterior of said annular valve body so as to have an interference fit within said circumferential groove.

12. A method in accordance with claim 2 wherein said valve body has a pair of diametrically opposed flat interior wall sections where said engaging means are located, which sections are located on opposite sides of said valve body along a diameter which is perpendicular to said diameter along which said compressive forces are applied.

13. A method in accordance with claim 1 wherein said oppositely directed compressive forces are applied via arcuate resilient pad means having curvature matched to the exterior radius of curvature of the exterior surface of said annular valve body.

14. A method in accordance with claim 13 wherein said arcuate pad means have rigid metal backing members of a curvature matched to that of the valve body in its distended condition and flexible pads which contact said exterior surface of said valve body, said flexible pads have a durometer value of between about 70 and about 90 and a thickness of at least about 0.05 cm.

15. A method of assembling a prosthetic heart valve having an annular valve body and at least one occluder which occluder interengages with support means formed on the interior surface of said valve body to support said occluder in a position to allow its movement between an open position and a closed position, which method comprises applying oppositely directed compressive forces to two exterior regions of the curvilinear exterior surface of said annular valve body which regions each extend for at least about 120° of arc and for an axial distance equal to at least about one-half the axial length of the valve body, said forces being applied over said at least about 120° of arc of said exterior surface regions and being of such a magnitude so as to distend said annular valve body from an unstressed generally circular annular configuration so as to elongate said body in regions where said occluder support means are located, while placing major exterior surface regions of said valve body in compression, installing said occluder in said distended valve body, and gradually removing said oppositely directed compressive forces to allow said valve body to return to its unstressed generally circular annular configuration with said occluder secured in interengagement within said valve body.

16. A method of assembling a prosthetic heart valve having a pair of occluders supported for pivotal movement between an open position and a closed position in an annular pyrocarbon valve body having an interior passageway of generally circular cross section for blood flow therethrough wherein slot means in the interior surface of said valve body support each said occluder for such pivotal movement, which method comprises distending said valve body by the application to the exterior surface of said valve body of two oppositely directed compressive forces, which forces are aligned along a diameter of said valve body located essentially perpendicular to a line interconnecting said valve body slot means for each said occluder, said forces being exerted over certain diametrically opposite arcuate surface regions of the exterior surface of said annular valve body each equal to at least about 60 degrees of arc so as to place said certain exterior surface regions in compression while distending said annular valve body from its unstressed generally circular configuration to cause said slot means to move sufficiently far apart from each other to permit each of said occluders to be installed, said oppositely directed compressive forces being applied via arcuate resilient pad means which contact said exterior surface of said valve body and which have rigid metal backing members of a curvature matched to that of said valve body in its distended condition, installing said occluders in said distended valve body so as to be supported by said slot means, and removing said oppositely directed compressive forces to permit said valve body to return to its unstressed generally circular configuration with said occluders operatively pivotally supported therewithin.

17. A method in accordance with claim 16 wherein said resilient pad means have a durometer value of between about 70 and about 90 and a thickness of at least about 0.05 cm.

18. A method in accordance with claim 16 wherein one of said metal backing members is stationary and the other backing member is movable.

19. A method in accordance with claim 18 which includes measuring the amount of said compressive force using load cell means associated with said stationary metal backing member to facilitate applying a certain amount of compressive force.

* * * * *